United States Patent
Yokoyama et al.

(10) Patent No.: US 6,515,142 B2
(45) Date of Patent: Feb. 4, 2003

(54) PROCESS FOR PREPARING 2-PHENYL-3-NAPHTHYLPROPIONIC ACID DERIVATIVES

(75) Inventors: Yukio Yokoyama, Tokyo (JP); Tatsuya Kobayashi, Tokyo (JP); Takeo Koyama, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/986,075

(22) Filed: Nov. 7, 2001

(65) Prior Publication Data

US 2002/0062033 A1 May 23, 2002

Related U.S. Application Data

(62) Division of application No. 09/742,348, filed on Dec. 22, 2000, now Pat. No. 6,337,405, which is a division of application No. 09/147,785, filed on Mar. 8, 1999, now Pat. No. 6,252,088, which is a continuation of application No. PCT/JP97/03125, filed on Sep. 5, 1997.

(30) Foreign Application Priority Data

| Sep. 6, 1996 | (JP) | 8-237013 |
| Sep. 6, 1996 | (JP) | 8-237014 |
| Mar. 12, 1997 | (JP) | 9-57357 |

(51) Int. Cl.$^7$ ............................................. C07D 207/08
(52) U.S. Cl. ........................ 548/531; 548/532; 548/546; 548/571
(58) Field of Search ................................. 548/532, 546, 548/531, 571

(56) References Cited

U.S. PATENT DOCUMENTS 5,620,991 A * 4/1997 Nagahara et al.
6,252,088 B1 * 6/2001 Yokoyama et al.
6,337,405 B1 * 1/2002 Yokoyama et al.

FOREIGN PATENT DOCUMENTS

| JP | 5-208946 | 8/1993 |
| JP | 6-227971 | 8/1994 |
| JP | 7-17937 | 1/1995 |

OTHER PUBLICATIONS

CAS online, 1995:294083, 123:285785, Ikeuchi et al., Japenese Patent 6–227971 (1994) RN: 150610–55–2 and RN: 150610–63–2.*

Takayasu Nagahara, et al. "Dibasic (Amidinoaryl)propanoic Acid Derivatives as Novel Blood Coagulation Factor Xa Inhibitors", J. Med. Chem., vol. 37, No. 8, pp. 1200–1207, 1994.

CAS online, 1995:294083, 123:285785, Ikeuchi et al., JP6–227971 (1994) RN:150610–55–2 and RN:150610–63–2.

* cited by examiner

*Primary Examiner*—Joseph K. McKane
*Assistant Examiner*—Sonya Wright
(74) *Attorney, Agent, or Firm*—Oblon, Spivak, McClelland, Maier & Neustadt, P.C.

(57) ABSTRACT

A process for preparing a compound represented by general formulae (5) and (6) in the following reaction scheme or salts thereof, wherein $R^1$ represents a protective group for a nitrogen atom; $R^2$ represents a methanesulfonyl group or p-toluenesulfonyl group; $R^1$ represents a hydrogen atom, an aralkyl group, or an alkyl group having 1 to 6 carbon atoms; and X represents a halogen atom.

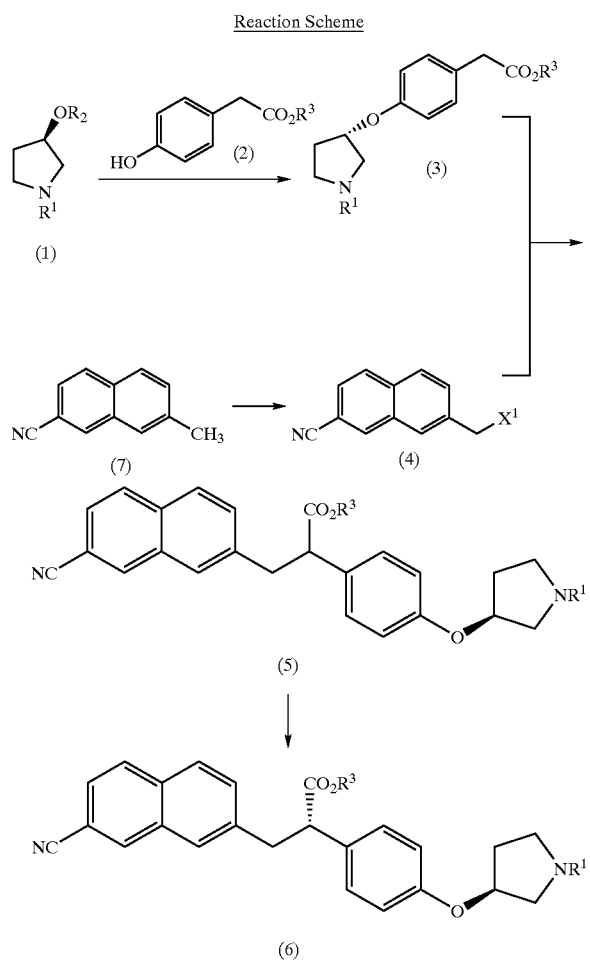

Reaction Scheme

The above process is useful as an industrial process for preparing intermediates of anticoagulant aromatic amidine derivatives described in Japanese Patent Application Laid-Open (kokai) No. 208946/1993.

16 Claims, No Drawings

PROCESS FOR PREPARING 2-PHENYL-3-NAPHTHYLPROPIONIC ACID DERIVATIVES

This application is a DIV of Ser. No. 09/742,348 filed Dec. 22, 2000, now U.S. Pat. No. 6,337,405 which is a DIV of Ser. No. 09/147,785 filed Mar. 8, 1999 now U.S. Pat. No. 6,252,088 which is a 371 of PCT/JP97/03125 filed Sep. 5, 1997.

TECHNICAL FIELD

The present invention relates to a process for preparing intermediates of aromatic amidine derivatives which have anticoagulation action based on excellent activated coagulation factor X (hereinafter abbreviated as FXa) inhibitory action and are described in Japanese Patent Application Laid-Open (kokai) No. 5-208946.

BACKGROUND ART

As intermediates of the aromatic amidine derivatives described in Japanese Patent Application Laid-Open (kokai) No. 5-208946, compounds of the following formulas (V), (Va), and (Vb), a nd salts thereof have conventionally been known:

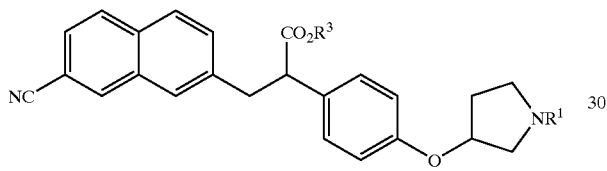
(V)

[wherein $R^1$ represents a protective group for a nitrogen atom and $R^3$ represents a hydrogen atom, an aralkyl group, or an alkyl group having 1 to 6 carbon atoms];

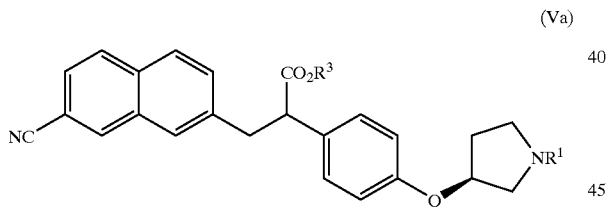
(Va)

[wherein $R^1$ and $R^3$ have the same meanings as described above]; and

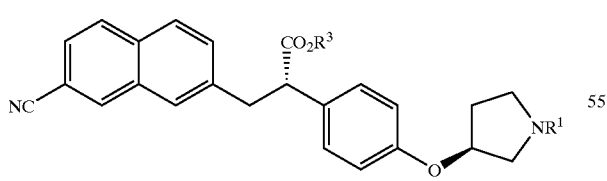
(Vb)

[wherein $R^1$ and $R^3$ have the same meanings as described above]. Processes for preparing the above compounds are also described in the cited publication.

A typical process for preparing these intermediates comprises the following steps:
brominating 7-methyl-2-naphthalenecarbonitrile to thereby form 7-Bromomethyl-2-naphthalenecarbonitrile (first step);

further converting the 7-Bromomethyl-2-naphthalenecarbonitrile to a phosphonium salt, [(7-cyano)-2-naphthyl)methyl]triphenylphosphonium bromide (second step);

synthesizing ethyl 2-[4-[[(3S)-1-(tert-Butoxycarbonyl)-3-hydroxypyrrolidinyl]oxylphenyl]-2-oxoacetate using a Mitsunobu reaction of ethyl 2-(4-hydroxyphenyl)-2-oxoacetate and (3R)-1-(tert-Butoxycarbonyl)-3-hydroxypyrrolidine (third step);

subjecting the obtained ethyl 2-[4-[[(3S)-1-(tert-Butoxycarbonyl)-3-hydroxypyrrolidinyl]oxy]phenyl]-2-oxoacetate and the [(7-cyano)-2-nahpthyl)methyl]-triphenylphosphonium bromide to a Wittig reaction (fourth step);

further performing catalytic hydrogenation to thereby form compounds represented by formula (V) or (Va) (fifth step); and dissolving compounds represented by formula (Va) in ethanol with heat, adding a small amount of sodium hydride thereto, and causing crystallization while stirring the mixture at room temperature, to thereby obtain compounds represented by formula (Vb) (sixth step).

However, the above-described prior art process has the following drawbacks:

1) bromination in the first step is performed in tetrachloromethane, which is a suspected carcinogen;
2) the product of the first step, i.e., 7-Bromomethyl-2-naphthalenecarbonitrile, causes skin irritation when isolated as crystals;
3) comparatively expensive reagents, diethyl azodicarboxylate and 1,8-diazabicyclo[5.4.0]-7-undecene, are used;
4) by-products formed both in the third step and the fourth step behave as catalyst poisons in the catalytic hydrogenation of the fifth step, and in order to remove the by-products, it requires purification by silica gel column chromatography;
5) palladium oxide monohydrate-barium sulfate, which is a catalyst of the catalytic hydrogenation, must be prepared upon use; and
6) the yield of the sixth step is low and sodium hydride, which involves a safety problem, is used.

Briefly, the prior art process is unsatisfactory as an industrial process.

Accordingly, an object of the present invention is to provide an industrially satisfactory process for preparing compounds represented by formulas (V), (Va), and (Vb) and salts thereof, by use of safe, inexpensive, and easily available starting material(s) and auxiliary material(s) and without a silica gel chromatographic purification step, as well as to provide an industrial process for preparing intermediates of aromatic amidine derivatives which are described in Japanese Patent Application Laid-Open (kokai) No. 5-208946.

DISCLOSURE OF THE INVENTION

In view of the foregoing, the present inventors have conducted earnest studies and have found that halogenation can be effectively performed in an alkylnitrile solvent in a first step, which permits the reaction to proceed to the next step without isolation of the product;

that use of a pyrrolidinyloxyphenylacetic acid derivative, obtained through condensation of 4-hydroxyphenylacetic acids and sulfonyloxypyrrolidines, as one starting material provides a compound represented by formula (V) or (Va) without requiring reaction to form a phosphonium salt and catalytic hydrogenation, and further without need for preparation of an expensive reagent or a reagent required upon use; and that applying a base to a diasteromeric mixture of compounds represented by formula (Va) results in easy formation of compounds represented by formula (Vb). The present invention was accomplished based on these findings.

The present invention is generally represented by the following reaction schemes I and II:

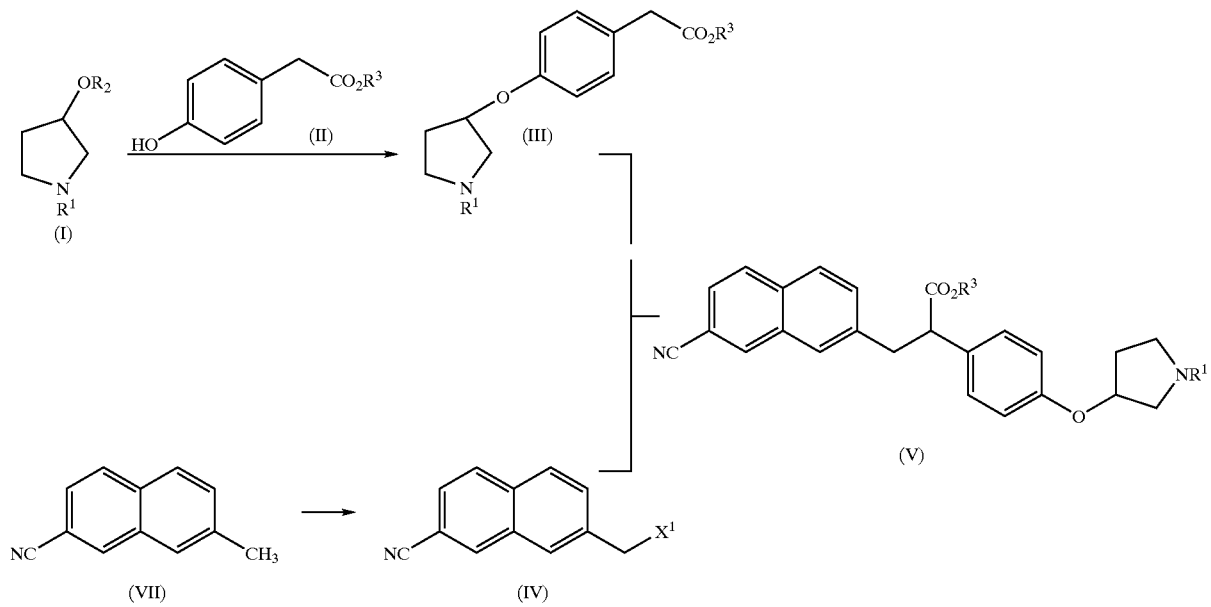

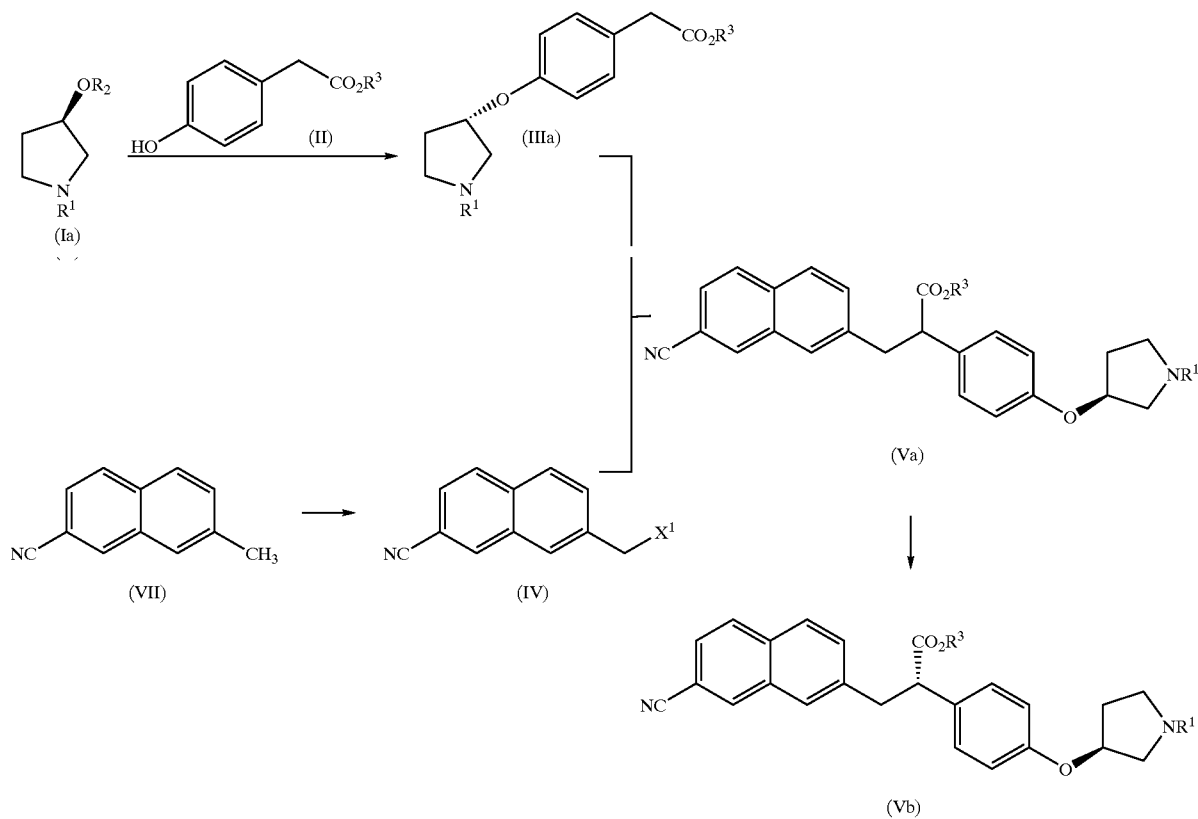

[(wherein $R^1$ represents a protective group for a nitrogen atom; $R^2$ represents a methanesulfonyl group or a p-toluenesulfonyl group; $R^3$ represents a hydrogen atom, an aralkyl group, or an alkyl group having 1 to 6 carbon atoms; and $X^1$ represents a leaving group].

Accordingly, the present invention provides a process for preparing a compound represented by formula (III) or (IIIa) or salts thereof through reaction of a compound represented by formula (I) or (Ia) and a compound represented by formula (II) in the presence of a base.

The present invention also provides a process for preparing a compound represented by formula (V) (or (Va)) or salts thereof through reaction of a compound represented by formula (III) (or (IIIa)) or a salt thereof and a compound represented by formula (IV) in the presence of a base.

The present invention further provides a process for preparing a compound represented by formula (Vb) through reaction of a compound represented by formula (Va) and a base.

The present invention still further provides a process for preparing a compound represented by formula (IVa):

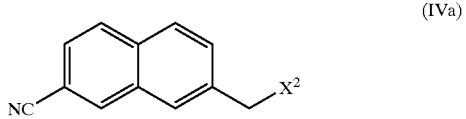

(IVa)

[wherein $X^2$ represents a halogen atom]; through halogenation of a compound represented by formula (VII) in an alkylnitrile solvent.

Of the compounds appearing in the above-described reaction schemes, some are novel compounds that have been newly found in the present invention. Accordingly, the present invention is also directed to such novel compounds which are useful as synthesis intermediates.

The present invention further provides compounds represented by formula (III):

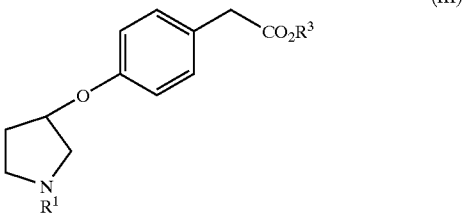

(III)

[(wherein $R^1$ and $R^2$ have the same meanings as described above], and salts thereof.

The present invention further provides compounds represented by formula (IIIa):

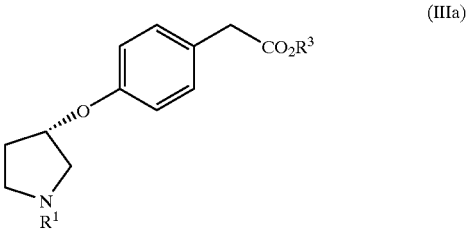

(IIIa)

[wherein $R^1$ and $R^3$ have the same meanings as described above], and salts thereof.

The present invention still further provides compounds represented by formula (Vc):

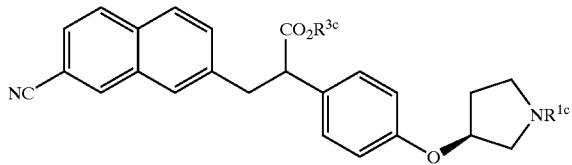

(Vc)

[wherein $R^{1c}$ represents a tertiary butoxycarbonyl group and $R^{3c}$ represents a hydrogen atom, an aralkyl group, or an alkyl group having 1 to 6 carbon atoms (other than an ethyl group)], and salts thereof.

The present invention yet further provides compounds represented by formula (Vd):

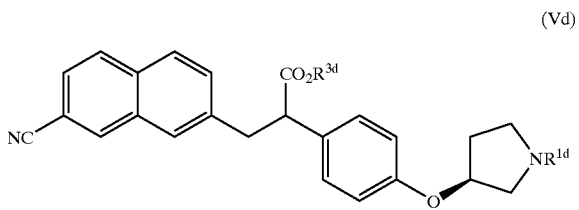

(Vd)

[wherein $R^{1d}$ represents a benzyl group and $R^{3d}$ represents a hydrogen atom, an aralkyl group, or an alkyl group having 1 to 6 carbon atoms], and salts thereof.

BEST MODE FOR CARRYING OUT THE INVENTION

The present will next be described in detail. Firstly, the substituents of the compounds according to the present invention are described.

$R^1$ represents a protective group for the nitrogen atom. Protective groups which are typically used may be employed for the protective group. Examples include a tert-butoxycarbonyl group, a benzyloxycarbonyl group, a p-nitrobenzyloxycarbonyl group, a benzyl group, a formyl group, an acetyl group, and a triphenylmethyl group. In the present invention, a tert-butoxycarbonyl group or a benzyl group is preferred.

$R^2$ represents a methanesulfonyl group or a p-toluenesulfonyl group.

The alkyl group having 1 to 6 carbon atoms represented by $R^3$ may be linear, branched, or cyclic, and examples thereof include a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, and a cyclohexyl group. The aralkyl group is a group formed of an alkyl group having 1 to 6 carbon atoms and an aryl group, and examples thereof include a benzyl group and a naphthylmethyl group. The group $R^3$ in the present invention is preferably an alkyl group having 1 to 6 carbon atoms, more preferably a methyl group or an ethyl group.

$X^1$ represents a leaving group. As the leaving group, any such a group which is usually used may be employed, and examples include a halogen atom, a methanesulfonyloxy group, and a p-toluenesulfonyloxy group. As used herein, examples of the halogen atom include a fluorine atom, a chlorine atom, a bromine atom, and an iodine atom. Of these, a bromine atom is particularly preferred.

$X^2$ represents a halogen atom. Examples of the halogen atom include a fluorine atom, a chlorine atom, a bromine atom, and an iodine atom. Among others, a bromine atom is preferred.

The compounds represented by formula (I) or formula (Ia), the compounds represented by formula (II), and the compounds represented by formula (VII) used in the present invention are easily available known compounds or compounds which can easily be produced according to literature.

The compounds represented by formula (I) are known compounds, and optically active (3R)-1-(tert-Butoxylcarbonyl)-3-methanesulfonyloxypyrrolidine (see Japanese Patent Application Laid-Open (kokai) No. 2-28180) and optically active (3R)-1-(tert-Butoxylcarbonyl)-3-p-toluenesulfonyloxypyrrolidine (see WO 9200295) represented by formula (Ia) are also known compounds.

Among the compounds represented by formula (II), methyl p-hydroxyphenylacetate and ethyl p-hydroxyphenylacetate are known compounds. Other p-hydroxyphenylacetic acid alkyl esters can easily be produced from the condensation use of the corresponding alcohol and easily available p-hydroxyphenylacetic acid.

7-Halomethyl-2-naphthalenecarbonitrile, which is an example compound of formula (IV), is also a known compound (Japanese Patent Application Laid-Open (kokai) Nos. 5-208946 and 7-17937).

The production process of the present invention will next be described in detail.

[Step A] Method for Preparing a Compound Represented by Formula (III) or Formula (IIIa) or Salts thereof:

In order to obtain a compound represented by formula (III) or formula (IIIa) or salts thereof, a compound represented by formula (I) or formula (Ia) is reacted with a compound represented by formula (II) in the presence of a base and optionally an catalyst.

No particular limitation is imposed on the solvent used in this step so long as it provides no adverse effect on the reaction. Examples of the solvent include organic solvents such as aprotic polar solvents, ethers, aromatic hydrocarbons, and alcohols; mixtures of the organic solvents; and mixtures of the organic solvents and water.

Examples of the aprotic polar solvents include N,N-dimethylformamide, N,N-dimethylacetamide, dimethyl sulfoxide, and acetonitrile. Examples of the ethers include tetrahydrofuran, dioxane, dimethoxyethane, diethylene glycol dimethyl ether, and triethylene glycol dimethyl ether. Examples of the aromatic hydrocarbons include benzene, toluene, and xylene. Examples of the alcohols include methanol and ethanol. Among the solvents, aprotic polar solvents or aromatic hydrocarbons are preferably used, with N,N-dimethylformamide or toluene being more preferred.

No particular limitation is imposed on the base so long as it provides no adverse effect on the reaction, and a weak or strong base may be used. Examples of a strong base include an alkali metal hydride such as sodium hydride or lithium hydride; an alkaline earth metal hydride such as calcium hydride; an alkali metal alkoxide such as sodium methoxide, lithium methoxide, sodium ethoxide, lithium ethoxide, sodium tert-butoxide, or potassium tert-butoxide; an alkali metal hydroxide such as sodium hydroxide or potassium hydroxide; and an alkali metal carbonate such as sodium carbonate or potassium carbonate. Strong bases are preferred. Particularly, an alkali metal hydride is preferred, with sodium hydride being more preferred.

Examples of the catalyst which is used in the present invention include phase-transfer catalysts and molecular sieves. Examples of the phase-transfer catalysts include oleophilic quaternary ammonium salts such as tetra(n-butyl) ammonium bromide, tetra(n-butyl)ammonium chloride, tetraethylammonium bromide, tetra(n-butyl)ammonium hydrogensulfide, triethylbenzylammonium bromide, or triethylbenzylammonium chloride; and crown ethers such as 18-crown-6,15-crown-5. Phase-transfer catalysts are preferred. Particularly, oleophilic quaternary ammonium salts are preferred, with tetra(n-butyl)ammonium bromide being more preferred. Addition of the catalysts increases the yield of the compounds represented by formula (III) or formula (IIIa) or salts thereof.

No particular limitation is imposed on the reaction temperature so long as it is not greater than the boiling point of the solvent. The reaction is typically performed within the temperature range from 0° C. to about the boiling point of the solvent used, preferably at 60° C.–110° C. The reaction time varies in accordance with the reaction temperature, and the reaction is performed typically for 15 minutes to one day, preferably for 4 hours or less.

[Step B] Method for Preparing a Compound Represented by Formula (IV):

The compound represented by formula (IV) may be obtained through a known method, and is preferably obtained through halogenation of a compound represented by formula (VII) in an alkylnitrile solvent. A radical initiator may be added during the halogenation.

No particular limitation is imposed on the alkylnitrile solvent so long as it provides no adverse effect on the reaction, and C2–C7 linear or branched alkylnitriles may be used. Examples of the C2–C7 linear or branched alkylnitriles include acetonitrile, propionitrile, n-butyronitrile, isobutyronitrile, valeronitrile, hexanenitrile, and heptanenitrile. Of these, linear or branched alkylnitriles having 2 to 4 carbon atoms such as acetonitrile, propionitrile, n-butyronitrile, or isobutyronitrile are preferred, with acetonitrile being more preferred.

No particular limitation is imposed on the radical initiator so long as it provides no adverse effect on the reaction, and examples thereof include peroxides such as dibenzoyl peroxide or azo compounds such as azobisisobutyronitrile. Instead of adding a radical initiator, operations such as light irradiation or heating may be performed. Of a variety of radical initoators, azo compounds are preferred, with 2,2'-azobisisobutyronitrile being particularly preferred.

The halogenation may be performed by adding a halogenating agent. No particular limitation is imposed on the halogenating agent so long as it provides no adverse effect on the reaction. Examples thereof include sulfuryl halides and N-halogenoimides. Of these, N-halogenoimides are preferred, with N-bromosuccinimide being more preferred.

No particular limitation is imposed on the reaction temperature so long as it is not higher than the boiling point of the solvent. The reaction is typically performed at 40° C.–120° C., preferably at about 80° C. The reaction time depends on the reaction temperature, and the reaction is typically performed for one hour to one day, preferably for 1–4 hours.

[Step C] Method for Preparing a Compound Represented by Formula (V) or Formula (Va) or Salts thereof:

In order to obtain a compound represented by formula (V) or formula (Va) or a salt thereof, a compound represented by formula (III) or formula (IIIa) is reacted with a compound represented by formula (IV) in the presence of a base.

No particular limitation is imposed on the solvent in the step so long as it provides no adverse effect on the reaction. Examples of the solvent include organic solvents such as aprotic polar solvents, ethers, esters, aromatic hydrocarbons, and alcohols; mixtures of the organic solvents; and mixtures of the organic solvents and water.

Examples of the aprotic polar solvents include N,N-dimethylformamide, N,N-dimethylacetamide, dimethyl sulfoxide, and acetonitrile. Examples of the ethers include tetrahydrofuran, dioxane, dimethoxyethane, diethylene glycol dimethyl ether, and triethylene glycol dimethyl ether. Examples of the esters include methyl acetate, ethyl acetate, methyl propionate, and ethyl propionate. Examples of the aromatic hydrocarbons include benzene, toluene, and xylene. Examples of the alcohols include methanol and ethanol. The mixtures of the organic solvents are preferably used. Of these, mixtures of an aprotic polar solvent and an aromatic hydrocarbon are preferred, with a mixture comprising N,N-dimethylformamide and toluene being more preferred.

No particular limitation is imposed on the base so long as it provides no adverse effect on the reaction, and a weak or strong base may be used. Examples of a strong base include an alkali metal hydride such as sodium hydride, or lithium hydride; an alkaline earth metal hydride such as calcium hydride; an alkali metal alkoxide such as sodium methoxide, lithium methoxide, sodium ethoxide, lithium ethoxide, sodium tert-butoxide, or potassium tert-butoxide; an alkali metal hydroxide such as sodium hydroxide or potassium hydroxide; and an alkali metal carbonate such as sodium carbonate or potassium carbonate. Strong bases are preferred. Particularly, an alkali metal hydride is preferred, with sodium hydride being more preferred.

No particular limitation is imposed on the reaction temperature so long as it is not higher than the boiling point of the solvent, however, the reaction is preferably performed at comparatively low temperature in order to suppress a side reaction. The reaction is performed typically within the temperature range from −10° C. to room temperature, preferably at 60° C.–110° C. The reaction time varies in accordance with the reaction temperature, and the reaction is performed typically for one hour to one day, preferably for 3–12 hours.

The thus-obtained 2-phenyl-3-naphthylpropionic acid derivatives, which are compounds represented by formula (V) or formula (Va), are important intermediates of aromatic amidine derivatives described in Japanese Patent Application Laid-Open (kokai) No. 5-208946.

Steps A and C; Steps B and C; or Steps A, B, and C may be performed continuously. Briefly, a compound represented by formula (III) or formula (IIIa) or a salt thereof that is obtained through Step A and a compound represented by formula (IV) or a salt thereof that is obtained through Step B may be used in the subsequent Step C without isolating the compounds at respective steps.

An example of the sequential steps will next be described. Firstly, in Step A, a compound represented by formula (III) or formula (IIIa) or a salt thereof is obtained through reaction in an aromatic hydrocarbon solvent by use of a phase-transfer catalyst in the presence of a strong base. Then, in Step B, a compound represented by formula (IV) obtained through reaction in an alkylnitrile is extracted with an aromatic hydrocarbon. Subsequently, a compound represented by formula (III) or formula (IIIa) or a salt thereof and a compound represented by formula (IV) are reacted, without isolating these compounds, in a solvent mixture comprising an aromatic hydrocarbon solvent containing an aprotic polar solvent in the presence of a strong base, to thereby obtain a compound represented by formula (V) or formula (Va) or a salt thereof.

The sequential steps requiring no operation such as isolation is preferred as an industrial process. In particular, since isolated crystals of 7-Bromomethyl-2-naphthalenecarbonitrile exhibit skin irritation, Step B and Step C are preferably performed sequentially.

(Step D] Method for Preparing an Optically Active Compound Represented by Formula (Vb):

In order to obtain a compound represented by formula (Vb) from a compound represented by formula (Va), a compound represented by formula (Va) may be reacted with a base.

Briefly, a compound represented by (Va) that is a mixture of an R-diastereomer and an S-diastereomer is reacted. with a base, to thereby obtain a compound represented by formula (Vb), which is an S-diastereomer.

Specifically, the R-diastereomer is dissolved in a solvent which is appropriate for inducing crystallization of the S-diastereomer and Is reacted in the dissolved state with a base, to thereby effect conversion from the R-diastereomer to the S-diastereomer. The target S-diastereomer Is then crystallized through the difference In solubility between the R-diastereomer and the S-diastereomer.

In this case, no particular limitation Is imposed on the solvent so long as it provides no adverse effect on the reaction, and there may be used a solvent which allows crystallization of compounds represented by formula (Vb). Specifically, protic solvents including water and alcohols may be used. These solvents may be used singly or in combination. The protic solvents may be blended with aprotic polar solvents, ethers, hydrocarbons, or mixtures thereof to thereby serve as a solvent.

Examples of the alcohols include methanol and ethanol. Examples of the aprotic polar solvents include N,N-dimethylformamide, dimethyl sulfoxide, and acetonitrile. Examples of the ethers include isopropyl ether, tetrahydrofuran, dioxane, dimethoxyethane, diethylene glycol dimethyl ether, and triethylene glycol dimethyl ether. Examples of the hydrocarbons include benzene, toluene, xylene, n-hexane, and n-pentane.

No particular limitation is imposed on the base so long as it provides no adverse effect on the reaction. Examples of the strong base include alkali metal alkoxides such as sodium methoxide, lithium methoxide, sodium ethoxide, lithium ethoxide, sodium tert-butoxide, or potassium tert-butoxide; alkali metal amides such as sodium amides; and alkali metal hydroxides such as sodium hydroxide or potassium hydroxide, and alkali metal carbonates such as sodium carbonate or potassium carbonate. Strong bases are preferably used. Of these, alkali metal alkoxides are preferred, with sodium ethoxide being more preferred.

The amount of the base is not limited so long as it provides no adverse effect on the reaction, and it is preferably 10–30% mol-equivalent based on the compound represented by formula (Va).

No particular limitation is imposed on the reaction temperature so long as it is not greater than the boiling point of the solvent. The reaction is performed typically in a temperature range from −10° C. to room temperature, preferably in a range from 10° C. to room temperature. The reaction time varies in accordance with the reaction temperature, and the reaction is performed typically for 30 minutes to several days, preferably for 20 hours or less.

The thus-obtained optically active 2-phenyl-3-naphthalenepropionic acid derivatives, which are compounds represented by formula (Vb), are important intermediates of aromatic amidine derivatives described in the cited reference.

The aromatic amidine derivatives or salts thereof may be prepared from compounds represented by formula (V), (Va), or (Vb) through a method described in Japanese Patent Application Laid-Open (kokai) No. 5-208946.

EXAMPLES

The present invention will next be described in detail by way of Examples, which should not be construed as limiting the invention thereto.

Example 1

Method for Preparing (3R)-1-Benzyl-3-methanesulfonyloxypyrrolidine (3R)-1-Benzyl-3-pyrrodinol (10.0 g, 56 mmol) and triethylamine (6.6 g, 65 mmol) were dissolved in toluene (100 ml), and the resultant solution was cooled to 5° C. Into this solution, methanesulfonyl chloride (7.1 g, 62 mmol) was added dropwise over 10 minutes at 5° C. After stirring the mixture for 30 minutes, toluene (100 ml) was added thereto, then the resultant solution was heated to room temperature and stirred for 1.5 hours. The reaction mixture was washed with saturated sodium bicarbonate water (200 ml), then with water (100 ml) twice. After concentration of the resultant organic layer under reduced pressure, the residue was subjected to silicagel column chromatography to yield 9.8 g of the title compound (yield: 68%).

Nuclear Magnetic Resonance Spectrum (CDCl$_3$) δ: 2.19 (1H, m), 2.30 (1H, m), 2.49 (1H, m), 2.76–2.89 (3H, m), 2.99 (3H, s), 3.64 (2H, dd, J=12.9, 12.9 Hz); 5.20 (1H, m), 7.25–7.35 (5H, m); Elementary Analysis C$_{12}$H$_{17}$NSO$_3$: Calculated: C, 56.45; H, 6.71; N, 5.49; Found: C, 55.70; H, 6.33; N, 5.48; FABMS (m/z): 256 (M$^+$+1); Infrared Absorption Spectrum νmax (KBr) cm$^{-1}$: 3028, 2944, 2804, 1496, 1454, 1356, 1170, 1146, 966; Angle of Rotation [α]$^{22}$D=+14.0° (c=1.0, MeOH).

Example 2

Method for Preparing 2-[4-[(3S)-1-(tert-Butoxycarbonyl)-3-pyrrolidinyl]oxy]phenylacetic Acid Ethyl Ester p-Hydroxyphenylacetic acid ethyl ester (39.6 g, 0.22 mol) was dissolved in dimethylformamide (500 ml). A solution of 60% sodium hydride (8.8 g, 0.22 mol) was added to the mixture at room temperature. Forty minutes later, (3R)-1-(tert-Butoxycarbonyl)-3-methanesulfonyloxypyrrolidine (53.1 g, 0.2 mol) was added thereto and heated for 15 minutes at an internal temperature of 110° C. The resultant mixture was cooled to room temperature, and concentrated by evaporating the solvent under reduced pressure. Acetic acid ethyl ester (500 ml) was added to the residue so as to dissolve the residue. The resultant solution was washed 4 times with aqueous 10% potassium hydroxide solution (100 ml). The organic layer was concentrated under reduced pressure, and the residue was subjected to silica gel column chromatography to yield 39.8 g of the title compound (yield: 57%).

Melting point: 39 to 40° C. Nuclear Magnetic Resonance Spectrum (CDCl$_3$) δ: 1.25 (3H, t, J=6.9 Hz) 1.47 (9H, s), 2.08–2.17 (2H, m), 3.46–3.63 (4H, m), 3.54 (2H, s), 4.14 (2H, q, J=6.9Hz), 4.86 (1H, m), 6.83 (2H, d, J=8.3Hz), 7.24 (2H, d, J=8.3 Hz); Elementary Analysis C$_{19}$H$_{26}$NO$_5$: Calculated: C, 65.31; H, 7.79; N, 4.01; Found: C, 65.20; H, 7.59; N, 3.76; MS (m/Z): 349 (M$^+$); Infrared Absorption Spectrum νmax (KBr) cm$^{-1}$: 2984, 1736, 1694, 1514, 1482, 1410, 1370, 1168, 1116; Angle of Rotation [α]$^{22}$D=+22.2° (c=1.0, CHCl$_3$).

Example 3

Method for Preparing 2-[4-[(3S)-1-(tert-Butoxycarbonyl)-3-pyrrolidinyl]oxy]phenylacetic Acid Ethyl Ester p-Hydroxyphenylacetic acid ethyl ester (39.6 g, 0.22 mol) was dissolved in dimethylformamide (500 ml), and then 60% sodium hydride (8.8 g, 0.22 mol) was added to the mixture at room temperature. Forty minutes later, (3R)-1-(tert-Butoxycarbonyl)-3-methanesulfonyloxypyrrolidine (53.1 g, 0.2 mol) was added thereto and the mixture was heated for 15 minutes at an internal temperature of 110° C. The resultant mixture was cooled to room temperature, and then was concentrated to remove the solvent under reduced pressure. Acetic acid ethyl ester (500 ml) was added to dissolve the residue, and the resultant solution was washed 4 times with 10% potassium hydroxide aqueous solution (100 ml). Analysis by reversed-phase chromatography by use of the obtained product from Example 2 as a standard sample revealed that 43.7 g of the title compound having a purity of 79% was obtained (62% yield).

Example 4

Method for Preparing 2-[4-[(3S)-1-(tert-Butoxycarbonyl)-3-pyrrolidinyl]oxy]phenylacetic Acid Ethyl Ester Procedures of Example 3 were repeated in dimethyl sulfoxide (25 ml) except that p-hydroxyphenylacetic acid ethyl ester (1.8 g, 10 mmol), (3R)-1-(tert-Butoxycarbonyl)-3-methanesulfonyloxy pyrrolidine (2.5 g, 10 mmol), and 60% sodium hydride (440 mg, 10 mmol) were used. Analysis by reversed-phase chromatography by use of the obtained product from Example 2 as a standard sample revealed that 1.8 g of the title compound was obtained (52% yield).

Example 5

Method for Preparing 2-[4-[(3S)-1-(tert-Butoxycarbonyl)-3-pyrrolidinyl]oxy]phenylacetic Acid Ethyl Ester Procedures of Example 3 were repeated in dimethylformamide (25 ml) except that p-hydroxyphenylacetic acid ethyl ester (1.8 g, 10 mmol), (3R)-1-(tert-Butoxycarbonyl)-3-methanesulfonyloxy pyrrolidine (2.5 g, 10 mmol), and sodium ethoxide (0.7 g, 10 mmol) were used. Analysis by reversed-phase chromatography by use of the obtained product from Example 2 as a standard sample revealed that 1.7 g of the title compound was obtained (50% yield).

Example 6

Method for Preparing 2-[4-[(3S)-1-(tert-Butoxycarbonyl)-3-pyrrolidinyl]oxy]phenylacetic Acid Ethyl Ester Procedures of Example 3 were repeated in dimethylformamide (25 ml) except that p-hydroxyphenylacetic acid ethyl ester (2.0 g, 11 mmol), (3R)-1-(tert-Butoxycarbonyl)-3-methanesulfonyloxy pyrrolidine (2.5 g, 10 mmol), and potassium tert-butoxide (1.2 g, 11 mmol) were used. Analysis by reversed-phase chromatography by use of the obtained product from Example 2 as a standard sample revealed that 2.0 g of the title compound was obtained (58% yield).

Example 7

Method for Preparing 2-[4-[(3S)-1-(tert-Butoxycarbonyl)-3-pyrrolidinyl]oxy]phenylacetic Acid Ethyl Ester Procedures of Example 3 were repeated in dimethylformamide (68 ml) except that p-hydroxyphenylacetic acid ethyl ester (4.0 g, 22 mmol), (3R)-1-(tert-Butoxycarbonyl)-3-p-toluenesulfonyloxy pyrrolidine (6.8 g, 20 mmol), and 60% sodium hydride (880 mg, 22 mmol) were used. Analysis by reversed-phase chromatography by use of the obtained product from Example 2 as a standard sample revealed that 4.4 g of the title compound was obtained (64% yield).

Example 8

Method for Preparing 2-[4-[(3S)-1-(tert-Butoxycarbonyl)-3-pyrrolidinyl]oxy]phenylacetic Acid Ethyl Ester p-Hydroxyphenylacetic acid ethyl ester (1.8 g, 10 mmol) was dissolved in ethanol (25 ml), and then sodium ethoxide (0.7 g, 10 mmol) was added to the mixture at room temperature. Forty minutes later, (3R)-1-(tert-Butoxycarbonyl)-3-methanesulfonyloxy pyrrolidine (2.5 g, 10 mmol) was added thereto and the mixture was subjected to heating and refluxing for 3 hours. The resultant mixture was cooled to room temperature, and then was concentrated to remove the solvent under reduced pressure. Acetic acid ethyl ester (30 ml) was added to dissolve the residue, and the resultant solution was washed 4 times with 10% potassium hydroxide aqueous solution (20 ml). Analysis by reversed-phase chromatography by use of the obtained product from Example 2 as a standard sample revealed that 0.9 g of the title compound was obtained (25% yield).

Example 9

Method for Preparing 2-[4-[(3S)-1-(tert-Butoxycarbonyl)-3-pyrrolidinyl]oxy]phenylacetic Acid Ethyl Ester Procedures of Example 8 were repeated in acetonitrile (26 ml) except that p-hydroxyphenylacetic acid ethyl ester (2.0 g, 11 mmol), (3R)-1-(tert-Butoxycarbonyl)-3-methanesulfonyloxy pyrrolidine (2.5 g, 10 mmol), and 60% sodium hydride (440 mg, 11 mmol) were used. Analysis by reversed-phase chromatography by use of the obtained product from Example 2 as a standard sample revealed that 2.2 g of the title compound was obtained (64% yield).

Example 10

Method for Preparing 2-[4-[(3S)-1-(tert-Butoxycarbonyl)-3-pyrrolidinyl]oxy]phenylacetic Acid Ethyl Ester p-Hydroxyphenylacetic acid ethyl ester (39.6 g, 0.22 mol) was dissolved in toluene (530 ml), and then 60% sodium hydride (8.8 g, 0.22 mol) was added to the mixture at room temperature. After heating the mixture at an internal temperature of 45° C. for one hour, (3R)-1-(tert-Butoxycarbonyl)-3-methanesulfonyloxy pyrrolidine (53.1 g, 0.2 mol) and tetranormalbutylammonium bromide (19.3 g, 60 mmol) were added thereto. The resultant mixture was heated at an internal temperature of 80° C. for 3 hours, and then was cooled to room temperature. The mixture was washed three times with 10% potassium hydroxide aqueous solution (106 ml). Analysis by reversed-phase chromatography by use of the obtained product from Example 2 as a standard sample revealed that 49.0 g of the title compound having a purity of 79% was obtained (70% yield).

Example 11

Method for preparing 7-Bromomethyl-2-naphthalene Carbonitrile 2,2'-azobisisobutyronitrile (982 mg, 6 mmol) and acetonitrile (100 ml) were added to 7-methyl-2-naphthalene carbonitrile (10.0 g, 60 mmol) at room temperature. N-bromosuccinimide (10.6 g, 60 mmol) was added thereto, and the mixture was subjected to heating and refluxing for 2 hours. The resultant mixture was cooled to room temperature. Water (100 ml) and toluene (100 ml) were added to the mixture for extraction. The resultant organic layer was washed twice with water (100 ml). After concentration of the organic layer under reduced pressure, the residue was subjected to silica-gel-column chromatography to yield 11.4 g of the title compound (78% yield). The data measured by instruments agreed with the data described in J. Med. Chem., 1991, 3105.

Example 12

Method for Preparing 7-Bromomethyl-2-naphthalene Carbonitrile 2,2'-azobisisobutyronitrile (982 mg, 6 mmol) and acetonitrile (100 ml) were added to 7-methyl-2-naphthalene carbonitrile (10.0 g, 60 mmol) at room temperature. N-bromosuccinimide (10.6 g, 60 mmol) was added thereto, and the mixture was subjected to heating and refluxing for 2 hours. The resultant mixture was cooled to room temperature. Water (100 ml) and toluene (100 ml) were added to the mixture for extraction. The resultant organic layer was washed twice with water (100 ml). After concentration of a part of the organic layer under reduced pressure, analysis of the residue by reversed-phase chromatography by use of the obtained product from Example 11 as a standard sample revealed that 12.1 g of the title compound was obtained (82% yield).

Example 13

Method for Preparing 7-Bromomethyl-2-naphthalene Carbonitrile 2,2'-azobisisobutyronitrile (491 mg, 3 mmol) and propionitrile (50 ml) were added to 7-methyl-2-naphthalene carbonitrile (5.0 g, 30 mmol) at room temperature. N-bromosuccinimide (5.3 g, 30 mmol) was added thereto, and the mixture was heated at an internal temperature of 80° C. for 4 hours. After that, the experiment was conducted in the same way as Example 12. Analysis by reversed-phase chromatography by use of the obtained product from Example 11 as a standard sample revealed that 1.9 g of the title compound was obtained (26% yield).

Example 14

Method for Preparing 7-Bromomethyl-2-naphthalene Carbonitrile 2,2'-azobisisobutyronitrile (491 mg, 3 mmol) and normal-butyronitrile (50 ml) were added to 7-methyl-2-naphthalene carbonitrile (5.0 g, 30 mmol) at room temperature. N-bromosuccinimide (5.3 g, 30 mmol) was added thereto, and the mixture was heated at an internal temperature of 80° C. for 2 hours. After that, the experiment was conducted in the same way as Example 12. Analysis by reversed-phase chromatography by use of the obtained product from Example 11 as a standard sample revealed that 5.4 g of the title compound was obtained (74% yield).

Example 15

Method for Preparing 7-Bromomethyl-2-naphthalene Carbonitrile 2,2'-azobisisobutyronitrile (491 mg, 3 mmol) and isobutyronitrile (50 ml) were added to 7-methyl-2-naphthalene carbonitrile (5.0 g, 30 mmol) at room temperature. N-bromosuccinimide (5.3 g, 30 mmol) was added thereto, and the mixture was heated at an internal temperature of 80° C. for 2 hours. After that, the experiment was conducted in the same way as Example 12. Analysis by reversed-phase chromatography, by use of the obtained product from Example 11 as a standard sample revealed that 4.3 g of the title compound was obtained (58% yield).

Example 16

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester 2-14-[(3S)-1-(tert-Butoxycarbonyl)-3-pyrrolidinyl] oxylphenylacetic acid ethyl ester (1.8 g, 5 mmol) obtained from Example 2 and 7-Bromomethyl-2-naphthalene carbonitrile (1.5 g, 6 mmol) were dissolved in dimethylformamide (15 ml), and the mixture was cooled to 0° C. Then, 60% sodium hydride (0.2 g, 5.5 mmol) was added thereto, and the mixture was stirred at the same temperature for 2.5 hours. The resultant mixture was diluted with acetic acid ethyl ester (30 ml), and was washed three times with water (10 ml). After concentration of the resultant organic layer under reduced pressure, the residue was subjected to silica-gel-column chromatography to yield 2.37 g of the title compound (89% yield). The data measured by instruments agreed with the data of Reference Example 35 described in Japanese Patent Application Laid-Open (kokai) No. 5-208946.

Example 17

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[(3S)-1-(tert-Butoxycarbonyl)-3-pyrrolidinyl]oxy] phenylacetic acid ethyl ester (40.0 g, 0.12 mol, purity: 79%) obtained from Example 3 and 7-Bromomethyl-2-naphthalene carbonitrile (33.8 g, 0.14 mol) were dissolved in dimethylformamide (340 ml), and the mixture was cooled to 0° C. Then, 60% sodium hydride (5.0 g, 0.13 mol) was added thereto, and the mixture was stirred at the same temperature for 3 hours. The resultant mixture was diluted with acetic acid ethyl ester (680 ml), and was washed three times with water (170 ml). Analysis by reversed-phase chromatography by use of the obtained product from Example 16 as a standard sample revealed that 54.1 g of the title compound having a purity of 66% was obtained (92% yield).

Example 18

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[(3S)-1-(tert-Butoxycarbonyl)-3-pyrrolidinyl]oxy] phenylacetic acid ethyl ester (40.0 g, 0.12 mol, purity: 79%) obtained from Example 10 and 7-Bromomethyl-2-naphthalene carbonitrile (33.8 g, 0.14 mol) were dissolved in dimethylformamide (400 ml), and the mixture was cooled to 0° C. Then, 60% sodium hydride (5.0 g, 0.13 mol) was added thereto, and the mixture was stirred at the same temperature for 3 hours. The resultant mixture was diluted with acetic acid ethyl ester (800 ml), and was washed three times with water (200 ml). Analysis by reversed-phase chromatography by use of the obtained product from Example 16 as a standard sample revealed that 53.5 g of the title compound having a purity of 67% was obtained (91% yield).

Example 19

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in dimethylformamide having 0.2% water (10 ml) except that 2-[4-[(3S)-1-(tert-Butoxycarbonyl)-3-pyrrolidinyl]oxy]phenylacetic acid ethyl ester (1.0 g, 2.8 mmol), 7-Bromomethyl-2-naphthalene carbonitrile (0.7 g, 2.8 mmol), and 60% sodium hydride (0.1 g, 3.1 mmol) were used. Analysis by reversed-phase chromatography by use of the obtained product from Example 16 as a standard sample revealed that 1.3 g of the title compound was obtained (90% yield).

Example 20

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in a mixture consisting of dimethylformamide (7.5 ml) and toluene (7.5 ml) except that 2-[4-[(3S)-1-(tert-Butoxycarbonyl)-3-pyrrolidinyl]oxy]phenylacetic acid ethyl ester (1.8 g, 5 mmol), 7-Bromomethyl-2-naphthalene carbonitrile (1.5 g, 6 mmol), and 60% sodium hydride (0.2 g, 5.5 mmol) were used. Analysis by reversed-phase chromatography by use of the obtained product from Example 16 as a standard sample revealed that 2.7 g of the title compound was obtained (92% yield).

Example 21

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in a mixture consisting of triethylene glycol dimethyl ether (9 ml) and toluene (9 ml) except that 2-[4-[(3S)-1-(tert-Butoxycarbonyl)-3-pyrrolidinyl]oxy]phenylacetic acid ethyl ester (1.8 g, 5 mmol), 7-Bromomethyl-2-naphthalene carbonitrile (1.5 g, 6 mmol), and 60% sodium hydride (0.2 g, 5.5 mmol) were used. Analysis by reversed-phase chromatography by use of the obtained product from Example 16 as a standard sample revealed that 1.8 g of the title compound was obtained (71% yield).

Example 22

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in triethylene glycol dimethyl ether (46 ml) except that 2-[4-[(3S)-1-(tert-Butoxycarbonyl)-3-pyrrolidinyl]oxy]phenylacetic acid ethyl ester (3.5 g, 10 mmol), 7-Bromomethyl-2-naphthalene carbonitrile (3.0 g, 12 mmol), and 60% sodium hydride (0.4g, 11 mmol) were used. Analysis by reversed-phase chromatography by use of the obtained product from Example 16 as a standard sample revealed that 4.4 g of the title compound was obtained (86% yield).

Example 23

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in dimethylformamide (15 ml) except that 2-[4-[(3S)-1-(tert-Butoxycarbonyl)-3-pyrrolidinyl]oxy]phenylacetic acid ethyl ester (1.7 g, 5 mmol), 7-Bromomethyl-2-naphthalene carbonitrile (1.5 g, 6 mmol), and sodium ethoxide (0.4 g, 5.5 mmol) were used. Analysis by reversed-phase chromatography by use of the obtained product from Example 16 as a standard sample revealed that 1.6 g of the title compound was obtained (65% yield).

Example 24

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in dimethylformamide (15 ml) except that 2-[4-[(3S)-1-(tert-Butoxycarbonyl)-3-pyrrolidinyl]oxy]phenylacetic acid ethyl ester (1.7 g, 5 mmol), 7-Bromomethyl-2-naphthalene carbonitrile (1.5 g, 6 mmol), and potassium tert-butoxide (0.6g, 5.5 mmol) were used. Analysis by reversed-phase chromatography by use of the obtained product from Example 16 as a standard sample revealed that 1.0 g of the title compound was obtained (38% yield).

Example 25

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in dimethylformamide (10 ml) except that 2-[4-[(3S)-1-(tert-Butoxycarbonyl)-3-pyrrolidinyl]oxy]phenylacetic acid ethyl ester (1.0 g, 2.8 mmol), 7-chloromethyl-2-naphthalene carbonitrile (0.6 g. 2.8 mmol), and sodium hydride (0.1 g, 3.1 mmol) were used. Analysis by reversed-phase chromatography by use of the obtained product from Example 16 as a standard sample revealed that 0.9 g of the title compound was obtained (61% yield).

Example 26

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 17 were repeated in dimethylformamide (10 ml) except that 2-[4-[(3S)-1-(tert-Butoxycarbonyl)-3-pyrrolidinyl]oxy]phenylacetic acid ethyl ester (1.0 g, 2.8 mmol), 7-p-toluenesulfonyloxymethyl-2-naphthalene carbonitrile (0.9 g, 2.8 mmol), and 60% sodium hydride (0.1 g, 3.1 mmol) were used. Analysis by reversed-phase chromatography by use of the obtained product from Example 16 as a standard sample revealed that 0.9 g of the title compound was obtained (64% yield).

Example 27

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester p-Hydroxyphenylacetic acid ethyl ester (1.4 g, 7.9 mmol) was dissolved in toluene (20 ml), and then 60% sodium hydride (310 mg, 7.9 mmol) was added to the mixture at room temperature. After heating the mixture at an internal temperature of 45° C. for one hour, (3R)-1-(tert-Butoxycarbonyl)-3-methanesulfonyloxy pyrrolidine (1.9 g, 7.1 mmol) and tetranormalbutylammonium bromide (690 mg, 2.4 mmol) were added thereto. The resultant mixture was heated at an internal temperature of 80° C. for 3 hours, and then was cooled to room temperature. The mixture was washed three times with 10% potassium hydroxide aqueous solution (4 ml). Analysis by reversed-phase chromatography by use of the obtained product from Example 2 as a standard sample revealed that 1.7 g of 2-[4-[(3S)-1-(tert-Butoxycarbonyl)-3-pyrrolidinyl]oxy]phenylacetic acid ethyl ester was obtained (70% yield).

Without concentration of the resultant organic layer, 7-Bromomethyl-2-naphthalenecarbonitrile (1.5 g, 6 mmol) and dimethylformamide (20 ml) were added to the organic layer, and the mixture was cooled to 0° C. Then, 60% sodium hydride (220 mg, 5.5 mmol) was added thereto, and the resultant mixture was stirred at the same temperature for 10 hours. The reaction mixture was washed three times with water (20 ml), and analysis by reversed-phase chromatography by use of the obtained product from Example 16 as a standard sample revealed that 2.4 g of the title compound was obtained (92% yield). The overall yield over the two steps was 64%.

Example 28

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester Procedures of Example 27 were repeated except that p-hydroxyphenylacetic acid ethyl ester (1.4 g, 7.9 mmol), toluene (20 ml), 60% sodium hydride (310 mg, 7.9 mmol), (3R)-1-(tert-Butoxycarbonyl)-3-methanesulfonyloxy pyrrolidine (1.9 g, 7.1 mmol) and tetranormalbutylammonium bromide (690 mg, 2.4 mmol) were used. The resultant organic layer was analyzed by reversed-phase chromatography by use of the obtained product from Example 2 as a standard sample revealed that 1.7 g of 2-[4-[(3S)-1-(tert-Butoxycarbonyl)-3-pyrrolidinyl]oxy]phenylacetic acid ethyl ester was obtained (70% yield).

Without concentration of the resultant organic layer, 7-Bromomethyl-2-naphthalenecarbonitrile (1.5 g, 6 mmol) and dimethylformamide (20 ml), and then 60% sodium hydride (220 mg, 5.5 mmol) were added thereto, and the resultant mixture was stirred at room temperature for 8 hours. The reaction mixture was washed three times with water (20 ml), and analysis by reversed-phase chromatography by use of the obtained product from Example 16 as a standard sample revealed that 2.3 g of the title compound was obtained (88% yield). The overall yield over the two steps was 61%.

Example 29

Method for Preparing 2-[4-[[(3S)-1-(tert-Butoxycarbonyl)-3-pyrrolidinyl]oxy]phenyl]-3-(7-cyano-2-naphthyl)propionic Acid Ethyl Ester 2,2'-azobisisobutyronitrile (624 mg, 3.8 mmol) and acetonitrile (65 ml) were added to 7-methyl-2-naphthalene carbonitrile (6.3 g, 38 mmol) at room temperature. N-bromosuccinimide (6.8 g, 38 mmol) was added thereto, and the mixture was subjected to heating and refluxing for 2 hours. The resultant mixture was cooled to room temperature. Water (65 ml) and toluene (65 ml) were added to the mixture, and the mixture was subjected to extraction. The resultant organic layer was washed twice with water (65 ml). Analysis by reversed-phase chromatography by use of the obtained product from Example 11 as a standard sample revealed that 7.4 g of 7-Bromomethyl-2-naphthalene carbonitrile was obtained (80% yield).

Without concentration of this organic layer, 2-[4-[(3S)-1-(tert-Butoxycarbonyl)-3-pyrrolidinyl]oxy]phenylacetic acid ethyl ester (8.7 g, 25 mmol, purity: 79%) obtained from Example 10, and dimethylformamide (81 ml) were added thereto, and the resultant mixture was cooled to 0° C. Then, 60% sodium hydride (1.1 g, 27.5 mmol) was added thereto, and the resultant mixture was stirred at the same temperature for 5 hours. The resultant solution was diluted with toluene (40 ml) and washed three times with water (80 ml). The resultant organic layer was concentrated under reduced pressure, and the residue (19.3 g) was analyzed by reversed-phase chromatography by use of the obtained product from Example 16 as a standard sample revealed that 11.7 g of the title compound was obtained (91% yield).

Example 30

Method for Preparing 2-[4-[[(3S)-1-(tert-Butoxycarbonyl)-3-pyrrolidinyl]oxy]phenyl]-3-(7-cyano-2-naphthyl)propionic Acid Methyl Ester 2-[4-[(3S)-1-(tert-Butoxycarbonyl)-3-pyrrolidinyl]oxy] phenylacetic acid methyl ester (1.7 g, 5 mmol), and 7-Bromomethyl-2-naphthalene carbonitrile (1.4 g, 5.5 mmol) were dissolved in dimethylformamide (15 ml), and the mixture was cooled to 0° C. Then, 60% sodium hydride (0.2 g, 5.5 mmol) was added thereto, and the resultant mixture was stirred at the same temperature for 3 hours. The resultant mixture was diluted with acetic acid ethyl ester (30 ml), and was washed three times with water (10 ml). The resultant organic layer was concentrated under reduced pressure, and the residue was subjected to silica-gel-column chromatography to yield 2.3 g of the title compound (93% yield).

Nuclear Magnetic Resonance Spectrum (CDCl$_3$) δ: 1.47 (9H, s), 2.14 (2H, m), 3.19 (1H, dd, J=6.9, 13.9 Hz), 3.55 (5H, m) 3.60 (3H, s), 3.90 (1H, br), 4.86 (1H, m) 6.83 (2H, d, J=8.6Hz), 7.23 (2H, d, J=8.3 Hz), 7.41 (1H, dd, J=1.5, 8.3 Hz), 7.56 (1H, dd, J=1.5, 8.3 Hz), 7.61 (1H, S), 7.78 (1H, d, J=8.3 Hz), 7.85 (1H, d, J=8.3 Hz), 8.13 (1H, s).

Example 31

Method for Preparing 2-[4-[[(3S)-1-(tert-Butoxycarbonyl)-3-pyrrolidinyl]oxy]phenyl]-3-(7-cyano-2-naphthyl)propionic Acid Isopropyl Ester 2-[4-[(3S)-1-(tert-Butoxycarbonyl)-3-pyrrolidinyl]oxy] phenylacetic acid isopropyl ester (1.8 g, 5 mmol), and 7-Bromomethyl-2-naphthalene carbonitrile (1.5 g, 6 mmol) were dissolved in dimethylformamide (15 ml), and the mixture was cooled to 0° C. Then, 60% sodium hydride (0.2 g, 5.5 mmol) was added thereto, and the resultant mixture was stirred at the same temperature for 5 hours. The resultant mixture was diluted with acetic acid ethyl ester (30 ml), and was washed three times with water (10 ml). The resultant organic layer was concentrated under reduced pressure, and the residue was subjected to silica-gel-column chromatography to yield 2.4 g of the title compound (92% yield).

Nuclear Magnetic Resonance Spectrum (CDCl$_3$) δ: 1.05 (3H, d, J=6.3 Hz), 1.08 (3H, d, J=5.6 Hz), 1.47 (9H, s), 2.14 (2H, m), 3.17 (1H, dd, J=6.6, 13.7 Hz), 3.55 (5H, m), 3.85 (1H, br), 4.86 (1H, m), 4.90 (1H, m), 6.83 (2H, d, J=8.6 Hz), 7.23 (2H, br), 7.42 (1H, d, J=8.3 Hz), 7.55 (1H, dd, J=1.6, 8.6 Hz), 7.62 (1H, s), 7.79 (1H, d, J=8.6 Hz), 7.84 (1H, d, J=8.6 Hz), 8.13 (1H, s).

Example 32

Method for Preparing 2-[4-[[(3S)-1-(tert-Butoxycarbonyl)-3-pyrrolidinyl]oxy]phenyl]-3-(7-cyano-2-naphthyl)propionic Acid Tert-butyl Ester 2-[4-[(3S)-1-(tert-Butoxycarbonyl)-3-pyrrolidinyl]oxy] phenylacetic acid tert-butyl ester (1.9 g, 5 mmol), and 7-Bromomethyl-2-naphthalene carbonitrile (1.5 g, 6 mmol) were dissolved in dimethylformamide (15 ml), and the mixture was cooled to 0° C. Then, 60% sodium hydride (0.2 g, 5.5 mmol) was added thereto, and the resultant mixture was stirred at the same temperature for 4 hours, followed by stirring at room temperature for four hours. The resultant mixture was diluted with acetic acid ethyl ester (30 ml), and was washed three times with water (10 ml). The resultant organic layer was concentrated under reduced pressure, and the residue was subjected to silica-gel-column chromatography to yield 2.1 g of the title compound (79% yield).

Nuclear Magnetic Resonance Spectrum (CDCl$_3$) δ: 1.30 (9H, s), 1.47 (9H, s), 2.13 (2H, m), 3.13 (1H, dd, J=6.6, 13.9 Hz), 3.52 (5H, m), 3.79 (1H, br) 4.87 (1H, m), 6.83 (2H, d, J=8.6 Hz), 7.21 (2H, d, J=8.3 Hz), 7.43 (1H, d, J=7.6 Hz), 7.55 (1H, d, J=7.6 Hz), 7.62 (1H, s), 7.77 (1H, d, J=8.6 Hz), 7.86 (1H, d, J=8.6 Hz), 8.13 (1H, s).

Example 33

Method for Preparing 2-[4-[[(3S)-1-(tert-Butoxycarbonyl)-3-pyrrolidinyl]oxy]phenyl]-3-(7-cyano-2-naphthyl)propionic Acid Benzyl Ester 2-[4-[(3S)-1-(tert-Butoxycarbonyl)-3-pyrrolidinyl]oxy] phenylacetic acid benzyl ester (2.1 g, 5 mmol), and 7-Bromomethyl-2-naphthalene carbonitrile (1.5 g, 6 mmol) were dissolved in dimethylformamide (15 ml), and the mixture was cooled to 0° C. Then, 60% sodium hydride (0.2 g, 5.5 mmol) was added thereto, and the resultant mixture was stirred at the same temperature for 3 hours. The resultant mixture was diluted with acetic acid ethyl ester (30 ml), and was washed three times with water (10 ml). The resultant organic layer was concentrated under reduced pressure, and the residue was subjected to silica-gel-column chromatography to yield 2.6 g of the title compound (90% yield).

Nuclear Magnetic Resonance Spectrum (CDCl$_3$) δ: 1.47 (9H, s), 2.11 (2H, m), 3.17 (1H, dd), 3.51 (5H, m), 3.93 (1H, br) 4.83 (1H, m), 4.92 (1H, d, J=13.2 Hz), 5.10 (1H, d, J=9.9 Hz), 6.83 (2H, d, J=8.6 Hz), 7.05–8.30 (7H, m), 7.39 (1H, d, J=8.2 Hz), 7.52 (1H, d, J=9.9 Hz), 7.55 (1H, s), 7.72 (1H, d, J=8.6 Hz), 7.83 (1H, d, J=8.6 Hz), 7.99 (1H, s).

Example 34

Method for Preparing 2-[4-[(3S)-1-Benzyl-3-pyrrolidinyl]oxy]phenylacetic Acid Ethyl Ester p-Hydroxyphenylacetic acid ethyl ester (9.1 g, 49.5 mmol) was dissolved in dimethylformamide (120 ml), and then 60% sodium hydride (2.0 g, 49.5 mmol) was added to the mixture at room temperature. After 40 minutes, (3R)-1-Benzyl-3-methanesulfonyloxy pyrrolidine (11.5 g, 45 mmol) was added thereto, and the resultant mixture was immediately heated in the oil bath maintained at 135° C.

After being heated at the internal temperature of 110° C. for 15 minutes, the mixture was cooled to room temperature. The mixture was then concentrated to remove the solvent under reduced pressure, and acetic acid ethyl ester (120 ml) was added to dissolve the residue. The resultant mixture was washed three times with 10% potassium hydroxide aqueous solution (24 ml). The resultant organic layer was concentrated under reduced pressure, and the residue was subjected to silica-gel-column chromatography to yield 10.9 g of the title compound (71% yield).

Nuclear Magnetic Resonance Spectrum (CDCl$_3$) δ: 1.24 (3H, t, J=6.9 Hz), 1.98 (1H, m), 2.29 (1H, m), 2.60 (1H, m), 2.74 (2H, m), 2.98 (1H, dd, 6.3, 6.3 Hz), 3.52 (2H, s), 3.67 (2H, dd, 12.9, 12.9 Hz), 4.13 (2H, q, J=6.9 Hz), 4.80 (1H, m), 6.78 (2H, d, J=8.6 Hz), 7.15 (2H, d, J=8.9 Hz), 7.24–7.35 (5H, m); Elementary Analysis C$_{21}$H$_{25}$NO$_3$: Calculated: C, 74.31; H, 7.42; N, 4.13; Found: C, 73.82; H, 7.36; N, 4.01. FABMS (m/Z): 340 (M$^+$+1); Infrared Absorption Spectrum νmax (KBr) cm$^{-1}$: 2984, 2800, 1732, 1614, 1512, 1296, 1244, 1148, 1028; Angle of Rotation [α]$^{24}$D=+ 7.8° (c=1.0, CHCl$_3$).

Example 35

Method for Preparing 2-[4-[(3S)-1-Benzyl-3-pyrrolidinyl]oxy]phenylacetic Acid Ethyl Ester p-Hydroxyphenylacetic acid ethyl ester (9.9 g, 55 mmol) was dissolved in dimethylformamide (120 ml), and then 60% sodium hydride (2.2 g, 55 mmol) was added to the mixture at room temperature. After 40 minutes, (3R)-1-Benzyl-3-methanesulfonyloxy pyrrolidine (12.8 g, 50 mmol) was added thereto, and the resultant mixture was immediately heated in the oil bath maintained at 135° C. After being heated at the internal temperature of 110° C. for 15 minutes, the mixture was cooled to room temperature. The mixture was then concentrated to remove the solvent under reduced pressure, and acetic acid ethyl ester (120 ml) was added to dissolve the residue. The resultant mixture was washed three times with 10% potassium hydroxide aqueous solution (24 ml). The resultant organic layer was concentrated under reduced pressure, and analysis of the residue by reversed-phase chromatography by use of the obtained product from Example 34 as a standard sample revealed that 12.2 g of the title compound was obtained (72% yield, purity: 82%).

Example 36

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (1.0 g, 3 mmol) obtained from Example 34 and 7-Bromomethyl-2-naphthalene carbonitrile (0.9 g, 3.6 mmol) were dissolved in dimethylformamide (10 ml), and the mixture was cooled to 0° C. Then, 60% sodium hydride (0.1 g, 3.3 mmol) was added thereto and the mixture was stirred at the same temperature for 1.5 hours. The resultant mixture was diluted with acetic acid ethyl ester (30 ml), and was washed three times with water (10 ml). After concentration of the resultant organic layer under reduced pressure, the residue was subjected to silica-gel-column chromatography to yield 0.3 g of the title compound (20% yield).

Nuclear Magnetic Resonance Spectrum (CDCl$_3$) δ: 1.10 (3H, t, J=6.9 Hz), 1.97 (1H, m), 2.28 (1H, m), 2.60 (1H, m), 2.74 (2H, m), 2.97 (1H, m), 3.16 (1H, dd, J=6.9, 13.5 Hz), 3.54 (1H, dd, J=8.9, 13.5 Hz), 3.67 (2H, dd, J=12.9, 12.9 Hz), 3.85 (1H, dd, J=6.9, 8.6 Hz), 3.99–4.13 (2H, m), 4.79 (1H, m), 6.76 (2H, d, J=8.6 Hz), 7.20 (2H, d, J=8.6 Hz), 7.23–7.34 (5H, m), 7.41 (1H, d, J=8.3 Hz), 7.54 (1H, dd, J=8.6, 8.6 Hz), 7.60 (1H, s), 7.76 (1H, d, J=8.6 Hz), 7.85 (1H, d, J=8.6 Hz), 8.11 (1H, s); Angle of Rotation [α]$^{22}$D=+ 3.9° (c=1.0, CHCl$_3$).

Example 37

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (500 mg, 1.5 mmol) was dissolved in dimethylformamide (5 ml), and the mixture was cooled to −10° C. Then, 60% sodium hydride (60 mg, 1.5 mmol) was added thereto and the mixture was stirred at the same temperature for 0.5 hours. After that, 7-Bromomethyl-2-naphthalene carbonitrile (370 mg, 1.5 mmol) was gradually added thereto, the resultant mixture was stirred at the same temperature for 4 hours. The resultant mixture was diluted with acetic acid ethyl ester (15 ml), and was washed three times with water (5 ml). After concentration of the resultant organic layer under reduced pressure, analysis by reversed-phase chromatography by use of the obtained product from Example 36 as a standard sample revealed that 480 mg of the title compound was obtained (64% yield).

Example 38

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (0.5 g, 1.5 mmol) and 7-Bromomethyl-2-naphthalene carbonitrile (440 mg, 1.8 mmol) were dissolved in dimethoxyethane (5 ml), and the mixture was cooled to 0° C. Then, 60% sodium hydride (66 mg, 1.65 mmol) was added thereto and the mixture was stirred at the same temperature for 5 hours. After that, procedures of Example 37 were repeated. Analysis by reversed-phase chromatography by use of the obtained product from Example 36 as a standard sample revealed that 158 mg of the title compound was obtained (21% yield).

Example 39

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (0.5 g, 1.5 mmol) and 7-Bromomethyl-2-naphthalene carbonitrile (440 mg, 1.8 mmol) were dissolved in diethylene glycol dimethyl ether (5 ml), and the mixture was cooled to 0° C. Then, 60% sodium hydride (66 mg, 1.65 mmol) was added thereto and the mixture was stirred at the same temperature for 5 hours. After that, procedures of Example 37 were repeated. Analysis by reversed-phase chromatography by use of the obtained product from Example 36 as a standard sample revealed that 555 mg of the title compound was obtained (73% yield).

Example 40

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (0.5 g, 1.5 mmol) and 7-Bromomethyl-2- naphthalene carbonitrile (440 mg, 1.8 mmol) were dissolved in triethylene glycol dimethyl ether (5 ml), and the mixture was cooled to 0° C. Then, 60% sodium hydride (66 mg, 1.65 mmol) was added thereto and the mixture was stirred at the same temperature for 6 hours. After that, procedures of Example 37 were repeated. Analysis by reversed-phase chromatography by use of the obtained product from Example 36 as a standard sample revealed that 647 mg of the title compound was obtained (85% yield).

Example 41

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (500 mg, 1.5 mmol) was dissolved in dimethylformamide (5 ml), and the mixture was cooled to −10° C. Then, sodium ethoxide (102 mg, 1.5 mmol) was added thereto and the mixture was stirred at the same temperature for 0.5 hours. Then, 7-Bromomethyl-2-naphthalene carbonitrile (370 mg, 1.5 mmol) was gradually added thereto, the resultant mixture was stirred at the same temperature for 3 hours. After that, procedures of Example 37 were repeated. Analysis by reversed-phase chromatography by use of the obtained product from Example 36 as a standard sample revealed that 332 mg of the title compound was obtained (44% yield).

Example 42

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (500 mg, 1.5 mmol) was dissolved in dimethylformamide (5 ml), and the mixture was cooled to -10° C. Then, sodium amide (60 mg, 1.5 mmol) was added thereto and the mixture was stirred at the same temperature for 0.5 hours. Then, 7-Bromomethyl-2-naphthalene carbonitrile (370 mg, 1.5 mmol) was gradually added thereto, the resultant mixture was stirred at the same temperature for 2 hours. After that, procedures of Example 37 were repeated. Analysis by reversed-phase chromatography by use of the obtained product from Example 36 as a standard sample revealed that 158 mg of the title compound was obtained (21% yield).

Example 43

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (500 mg, 1.5 mmol) and 7-chloromethyl-2-naphthalene carbonitrile (363 mg, 1.8 mmol) were dissolved in dimethylformamide(5 ml), and the mixture was cooled to 0° C. Then, 60% sodium hydride (66 mg, 1.65 mmol) was added thereto and the mixture was stirred at the same temperature for 3 hours. After that, procedures of Example 37 were repeated. Analysis by reversed-phase chromatography by use of the obtained product from Example 36 as a standard sample revealed that 473 mg of the title compound was obtained (62% yield).

Example 44

Method for Preparing 2-[4-[[(3S)-1-Benzyl-3-pyrrolidinyl]oxy]phenyl]-3-(7-cyano-2-naphthyl) propionic Acid Ethyl Ester 2-[4-[(3S)-1-Benzyl-3-pyrrolidinyl]oxy]phenylacetic acid ethyl ester (5.4 g, 16 mmol, purity: 82%) and 7-Bromomethyl-2-naphthalene carbonitrile (4.7 g, 19.2 mmol) were dissolved in triethyleneglycol dimethyl ether (54 ml), and the mixture was cooled to 0° C. Then, 60% sodium hydride (704 mg, 17.6 mmol) was added thereto, and the mixture was stirred at the same temperature for 8 hours. The resultant mixture was diluted with acetic acid ethyl ester (108 ml), and was washed three times with water (216 ml). After concentration of the resultant organic layer under reduced pressure, analysis by reversed-phase chromatography by use of the obtained product from Example 36 as a standard sample revealed that 6.4 g of the title compound was obtained (79% yield).

Example 45

Method for Preparing (2S)-2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[[(3S)-1-(tert-Butoxycarbonyl)-3-pyrrolidinyl]oxy]phenyl]-3-(7-cyano-2-naphthyl)propionic acid ethyl ester (54.1 g, 0.11 mol, purity: 66%) obtained from Example 17 was heated and dissolved in ethanol (180 ml), and the resultant mixture was cooled to room temperature with stirring to settle crystals. Subsequently, sodium ethoxide (1.1 g, 15.8 mmol) was added thereto, followed by stirring at the same temperature for 30 minutes, then sodium ethoxide (1.1 g, 15.8 mmol) was further added, followed by stirring for 18 hours. The crystals were collected through filtration, and washed with ethanol (55 ml). The crystals were found to have a diastereomer purity of 94.7% under HPLC analysis conditions of Reference Example 49 described in Japanese Patent Application Laid-Open (kokai) No. 5-208946. The crystals were dissolved in acetic acid ethyl ester (1228 ml), and washed three times with water (250 ml). The resultant organic layer was concentrated under reduced pressure, and the residue was recrystallized from ethanol (550 ml) to obtain 47.6 g of the title compound (88% yield). The data measured by instruments agreed with the data of Reference Example 49 described in Japanese Patent Application Laid-Open (kokai) No. 5-208946. The diastereomer purity of the crystals was 99.5%.

Example 46

Method for Preparing (2S)-2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[[(3S)-1-(tert-Butoxycarbonyl)-3-pyrrolidinyl]oxy]phenyl]-3-(7-cyano-2-naphthyl)propionic acid ethyl ester (50.0 g, 0.10 mol, purity: 67%) obtained from Example 18 was heated and dissolved in ethanol (165 ml), and the resultant solution was cooled to room temperature with stirring to settle crystals. Subsequently, sodium ethoxide (1.0 g, 14.6 mmol) was added thereto, followed by stirring at the same temperature for 30 minutes, then sodium ethoxide (1.0 g, 14.6 mmol) was further added, followed by stirring for 18 hours. The crystals were collected through filtration, and washed with ethanol (50 ml). The crystals were found to have a diastereomer purity of 93.5%. The crystals were dissolved in acetic acid ethyl ester (1900 ml), and washed three times with water (240 ml). The organic layer was concentrated under reduced pressure, and the residue was recrystallized from ethanol (500 ml) to obtain 43.8 g of the title compound (884 yield). The diastereomer purity of the crystals was 99.6%.

Example 47

Method for Preparing (2S)-2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[[(3S)-1-(tert-Butoxycarbonyl)-3-pyrrolidinyl]oxy]phenyl]-3-(7-cyano-2-naphthyl)propionic acid ethyl ester (11.3 g, 21.9 mmol, purity: 61%) obtained from Example 29 was heated and dissolved in ethanol (40 ml), and the resultant solution was cooled to room temperature with stirring to settle crystals. Subsequently, sodium ethoxide (235 mg, 3.28 mmol) was added thereto, followed by stirring at the same temperature for 30 minutes, then sodium ethoxide (235 mg, 3.28 mmol) was further added, and followed by stirring for 18 hours. The crystals were collected through filtration, and were washed with ethanol (10 ml). The obtained crystals had a diastereomer purity of 92.8%. The crystals were dissolved in acetic acid ethyl ester (250 ml), and washed three times with water (50 ml). The resultant organic layer was concentrated under reduced pressure, and the residue was recrystallized twice from ethanol (120 ml, 100 ml) to obtain 9.23 g of the title compound (82% yield). The diastereomer purity of the crystals was 99.8%.

Example 48

Method for Preparing (2S)-2-[4-[[(3S)-1-(tert-Butoxycarbonyl)-3-pyrrolidinyl]oxy]phenyl]-3-(7-cyano-2-naphthyl)propionic Acid Ethyl Ester 2-[4-[[(3S)-1-(tert-Butoxycarbonyl)-3-pyrrolidinyl]oxy]phenyl]-3-(7-cyano-2-naphthyl)propionic acid ethyl ester (1.90 g, 3.7 mmol) was heated and dissolved in ethanol (6 ml), and the resultant solution was cooled to room temperature with stirring to settle crystals. Subsequently, sodium amide (22 mg, 0.6 mmol) was added thereto, followed by stirring at the same temperature for 30 minutes, then sodium amide (22 mg, 0.6 mmol) was further added, followed by stirring for 18 hours. The crystals were collected through filtration to obtain 1.48 g of the title compound (78% yield). The diastereomer purity of the crystals was 92.3%.

Example 49

Method for Preparing (2S)-2-[4-[[(3S)-1-Benzyl-3-pyrrolidinyl]oxy]phenyl]-3-(7-cyano-2-naphthyl) propionic Acid Ethyl Ester 2-[4-[[(3S)-1-Benzyl-3-pyrrolidinyl]oxy]phenyl]-3-(7-cyano-2-naphthyl)propionic acid ethyl ester (5 g, 9.9 mmol) was heated and dissolved in ethanol (25 ml), and the resultant solution was cooled to room temperature with stirring to settle crystals. Subsequently, sodium ethoxide (100 mg, 1.5 mmol) was added thereto, followed by stirring at the same temperature for one hour, then sodium ethoxide (100 mg, 1.5 mmol) was further added, followed by stirring for 15 hours. The crystals were collected through filtration to obtain 3.3 g of the title compound (66% yield). The obtained crystals had a diastereomer purity of 82% under HPLC analysis conditions. The crystals were dissolved in acetic acid ethyl ester (75 ml), and washed three times with water (50 ml). The resultant organic layer was concentrated under reduced pressure, and the residue was recrystallized twice from ethanol (31 ml, 23 ml) to obtain 2.1 g of the title compound (43% yield). The diastereomer purity of the crystals was 99.1%.

Melting point: 95.0 to 95.5° C. Nuclear Magnetic Resonance Spectrum (CDCl$_3$) δ: 1.10 (3H, t, J=6.9 Hz), 1.98 (1H, m), 2.28 (1H, m), 2.60 (1H, m), 2.74 (2H, m), 2.98 (1H, dd, J=6.9, 8.6 Hz), 3.16 (1H, dd, J=6.9, 13.5 Hz), 3.54 (1H, dd, J=8.6, 13.5 Hz), 3.67 (2H, dd, J=12.9, 12.9Hz), 3.85 (1H, dd, J=6.9, 8.6 Hz), 3.96–4.12 (2H, m), 4.79 (1H, m), 6.76 (2H, d, J=8.6 Hz), 7.19 (2H, d, J=8.9 Hz), 7.24–7.35 (5H, m), 7.41 (1H, dd, J=8.3, 8.6 Hz), 7.54 (1H, dd, J=8.3, 8.6 Hz), 7.60 (1H, s), 7.71 (1H, d, J=8.6 Hz), 7.84 (1H, d, J=8.6 Hz), 8.11 (1H, s); Elementary Analysis C$_{33}$H$_{32}$N$_2$O$_4$: Calculated: C, 78.55; H, 6.39; N, 5.55, Found: C, 78.40; H, 6.48; N, 5.35, MS (m/Z): 504 (M$^+$); Infrared Absorption Spectrum vmax (KBr) cm$^{-1}$: 2800, 2232, 1730, 1610, 1512, 1254, 1156, 850; Angle of Rotation $[\alpha]^{22}$D=+112.5° (c=1.0, CHCl$_3$).

Example 50

Method for Preparing (2S)-2-[4-[[(3S)-1-Benzyl-3-pyrrolidinyl]oxy]phenyl]-3-(7-cyano-2-naphthyl) propionic Acid Ethyl Ester 2-[4-[[(3S)-1-Benzyl-3-pyrrolidinyl]oxy]phenyl]-3-(7-cyano-2-naphthyl)propionic acid ethyl ester (5 g, 9.9 mmol) was heated and dissolved in ethanol (50 ml), and the resultant solution was cooled to room temperature with stirring to settle crystals. Subsequently, sodium ethoxide (100 mg, 1.5 mmol) was added thereto, followed by stirring at the same temperature for one hour, then sodium ethoxide (100 mg, 1.5 mmol) was further added, followed by stirring for 15 hours. The crystals were collected through filtration to obtain 2.9 g of the title compound (58% yield). The crystals had a diastereomer purity of 84% under HPLC analysis conditions. The crystals were dissolved in acetic acid ethyl ester (66 ml), and washed three times with water (50 ml). The resultant organic layer was concentrated under reduced pressure, and the residue was recrystallized twice from ethanol (14.5 ml, 12 ml) to obtain 2.0 g of the title compound (40% yield). The diastereomer purity of the crystals was 93%.

Example 51

Method for Preparing (2S)-2-[4-[[(3S)-1-Benzyl-3-pyrrolidinyl]oxy]phenyl]-3-(7-cyano-2-naphthyl) propionic Acid Ethyl Ester 2-[4-[[(3S)-1-Benzyl-3-pyrrolidinyl]oxy]phenyl]-3-(7-cyano-2-naphthyl)propionic acid ethyl ester (5 g, 9.9 mmol) was heated and dissolved in ethanol (15 ml), and the resultant solution was cooled to room temperature with stirring to settle crystals. Subsequently, sodium ethoxide (100 mg, 1.5 mmol) was added thereto, followed by stirring at the same temperature for one hour, then sodium ethoxide (100 mg, 1.5 mmol) was further added, followed by stirring for 15 hours. The crystals were collected through filtration to obtain 3.9 g of the title compound (77% yield). The obtained crystals had a diastereomer purity of 47% under HPLC analysis conditions.

Industrial Applicability:

The present invention provides a process for preparing 2-phenyl-3-naphthylpropionic acid derivatives and optically active compounds thereof which play important roles as intermediates in manufacturing aromatic amidine derivatives having anticoagulation action based on excellent activated coagulation factor X. The process of the present invention is not only operationally simpler, but also costly advantageous. Thus, the process of the present invention is operationally and economically satisfactory as a useful process for industrial manufacture.

What is claimed is:

1. A process for preparing a compound of Formula (V) or a salt thereof:

(V)

wherein R¹ represents a protective group for a nitrogen atom and R³ represents a hydrogen atom, an aralkyl group, or an alkyl group having 1 to 6 carbon atoms, comprising:

reacting a compound of Formula (III):

(III)

with a compound of Formula (IVa)

(IVa)

in the presence of a base;
wherein in Formula (III) $R^1$ represents a protective group for a nitrogen atom and $R^3$ represents a hydrogen atom, an aralkyl group, or an alkyl group having 1 to 6 carbon atoms; and
wherein in Formula (IVa) $X^2$ is a halogen atom;
wherein the compound of formula (IVa) is obtained by a process comprising:
halogenating a compound of formula (VII):

(VII)

in an alkylnitrile solvent.

2. The process according to claim 1, wherein the reaction between a compound of formula (IVa) and a compound of formula (III) is performed in a solvent mixture of an aromatic hydrocarbon and an aprotic polar solvent, and the aromatic hydrocarbon is an extraction solvent for taking up the compound of formula (IVa) from the reaction mixture which has undergone halogenation reaction.

3. The process according to claim 2, wherein the aromatic hydrocarbon is toluene.

4. The process according to claim 2, wherein the solvent mixture of an aprotic polar solvent and an aromatic hydrocarbon is a mixture of N,N-dimethylformamide and toluene.

5. A process for preparing a compound of Formula (Va) or a salt thereof:

(Va)

wherein $R^1$ represents a protective group for a nitrogen atom and $R^3$ represents a hydrogen atom, an aralkyl group, or an alkyl group having 1 to 6 carbon atoms, comprising:

reacting a compound of Formula (IIIa):

(IIIa)

with a compound of Formula (IVa)

(IVa)

in the presence of a base;
wherein in Formula (III) $R^1$ represents a protective group for a nitrogen atom and $R^3$ represents a hydrogen atom, an aralkyl group, or an alkyl group having 1 to 6 carbon atoms; and
wherein in Formula (IVa) $X^2$ is a halogen atom;
wherein the compound of formula (IVa) is obtained by a process comprising:
halogenating a compound of formula (VII):

(VII)

in an alkylnitrile solvent.

6. The process according to claim 5, wherein the reaction between the compound of formula (IVa) and the compound of formula (IIIa) is performed in a solvent mixture of an aromatic hydrocarbon and an aprotic polar solvent, and the aromatic hydrocarbon is an extraction solvent for taking up the compound of formula (IVa) from the reaction mixture which has undergone halogenation reaction.

7. The process according to claim 6, wherein the aromatic hydrocarbon is toluene.

8. The process according to claim 6, wherein the solvent mixture of an aromatic hydrocarbon and an aprotic polar solvent is a mixture of N,N-dimethylformamide and toluene.

9. The process according to claim 1, wherein the alkylnitrile solvent is acetonitrile.

10. The process according to claim 1, wherein said halogenating is performed by the addition of a halogenating agent.

11. The process according to claim 10, wherein said halogenating agent is N-bromosuccinimide.

12. The process according to claim 1, wherein a radical initiator is 2,2'-azobisisobutyronitrile.

13. The process according to claim 5, wherein the alkylnitrile solvent is acetonitrile.

14. The process according to claim 5, wherein said halogenating is performed by the addition of a halogenating agent.

15. The process according to claim 14, wherein said halogenating agent is N-bromosuccinimide.

16. The process according to claim 5, wherein a radical initiator is 2,2'-azobisisobutyronitrile.

* * * * *